United States Patent [19] [11] 4,127,613
O'Neill [45] Nov. 28, 1978

[54] STABILIZATION OF METHYL TRIFLUOROVINYL ETHER

[75] Inventor: Gerald J. O'Neill, Arlington, Mass.

[73] Assignee: W. R. Grace & Co., Cambridge, Mass.

[21] Appl. No.: 843,988

[22] Filed: Oct. 20, 1977

[51] Int. Cl.$^2$ ............................................. C07C 41/12
[52] U.S. Cl. ................................................... 568/581
[58] Field of Search ............. 260/611.5, 652.5, 610 A, 260/610 SK

[56] References Cited
U.S. PATENT DOCUMENTS

| 3,557,009 | 1/1971 | McCloskey et al. ............ 260/610 X |
| 3,649,546 | 3/1972 | McCloskey et al. ............ 260/610 X |

OTHER PUBLICATIONS

Chem. Engineering & News, Apr. 12, 1976, p. 5.

Primary Examiner—Bernard Helfin
Attorney, Agent, or Firm—Lowell H. McCarter; C. Edward Parker

[57] ABSTRACT

Methyl trifluorovinyl ether can be stabilized with respect to liquid and vapor phase deflagration or explosive potential by the addition of certain fluorohaloalkanes to the methyl trifluorovinyl ether.

10 Claims, No Drawings

STABILIZATION OF METHYL TRIFLUOROVINYL ETHER

BACKGROUND OF THE INVENTION

The process of manufacturing vinyl ethers having the structure R—O—CF = CF$_2$ where R is alkyl, fluoro alkyl, or alkenyl group is described and claimed in U.S. Pat. No. 2,917,548. The compounds of the structure R—O—CF = CF$_2$ are monomers capable of being converted to useful polymers and other products. The use of the perfluorovinyl ethers in preparation of polymer products are described in U.S. Pat. Nos. 3,129,248; 3,133,046 and 3,159,609. More recently methyl trifluorovinyl ether has been used as a starting compound in manufacturing methylcyclopropyl ethers as described in U.S. Pat. Nos. 3,906,111 and 3,928,468.

The chemical industry has been recently informed of the explosive potential of these ethers. See Chem. Engineering & News, Apr. 12, 1976, pg. 5. Igniting the methyl trifluorovinyl ether by hot wire or an electric spark causes it to decompose violently with a substantial and rapid temperature and pressure rise. Under equivalent initial conditions of loading, vapor phase methyl trifluorovinyl ether appears to have a far greater explosive potential than does acetylene. Therefore all vinyl ethers having the above structure should be treated with extreme caution.

SUMMARY OF THE INVENTION

It has been found that methyl perfluorovinyl ether may be stabilized with respect to explosive potential by mixing with the methyl perfluorovinyl ether, one or more fluorohaloalkanes wherein the fluorohaloalkanes have a vapor pressure at least as large as the methyl perfluorovinyl ether. More particularly the admixture should contain a weight ratio of the fluorohaloalkanes to the methyl perflorovinyl ether of 1:1 or greater.

DESCRIPTION OF THE INVENTION

Methyl trifluorovinyl ether has been shown to be unstable material which can decompose violently when initiated by a suitable energy source. I have found that the addition of certain fluorohaloalkanes to the ether stabilizes both the liquid and vapor phases of the ether.

Tests carried out show that the methyl trifluorovinyl ether decomposition can be initiated in the vapor or liquid phase by a spark. I have found that adding dichlorofluoromethane (b.p. 8.9° C.), 1,2-dichloro-1,1,2,2-tetrafluoroethane (b.p. 3.8° C.), dichlorodifluoromethane (b.p. −29.8° C.), pentafluorochloroethane (b.p. −38.7° C.), chlorodifluoromethane (b.p. −40.8° C.), trifluorobromomethane (b.p. −57.8° C.), trifluorochloromethane (b.p. −81.4° C.), and mixtures thereof to the methyl trifluorovinyl ether (b.p. 10.5° C.) in a weight ratio of 1:1 or greater that both the liquid and vapor phases of the ether are unaffected by an electric spark.

Dichlorofluoromethane and 1,2-dichloro-1,1,2,2-tetrafluoroethane are the preferred fluorohaloalkanes since their boiling points are similar to the boiling point of methyl trifluorovinyl ether. The preferred fluorohaloalkanes can be used in systems cooled to about 0° C. at atmospheric pressure. The other fluorohaloalkanes are useful in systems at elevated pressures or at lower temperatures. Fluorohaloalkanes having appreciably higher boiling points are unsatisfactory.

The use of trichlorofluoromethane (b.p. 23° C.) in admixture with the ether stablizes the liquid but not the vapor. This may be due to the fact that the trichlorofluoromethane has a boiling point of 23° C. while the methyl trifluorovinyl ether has a boiling point of about 11° C. Thus trichlorofluoromethane has a lower vapor pressure under the test conditions resulting in a lower trichlorofluoromethane concentration in the vapor phase. The vapor above the mixture was ignited but the ignition was not transmitted to the liquid.

For the greatest effectiveness, the fluorohaloalkanes used should have at least as large a vapor pressure as the methyl trifluorovinyl ether. In a pressurized system the vapor pressure of the fluorohaloalkanes could be considerably higher. This insures that a different temperatures the concentration of the fluorohaloalkanes in the liquid and vapor phases will remain within the limits required for stabilization. Fluorohaloalkanes other than those enumerated above can also be used so long as they are not flammable and have suitable vapor pressures. The vapor pressure should be such that when the liquids — methyl rifluorovinyl ether and fluorohaloalkane — are combined in the preferred proportions the concentration of the inhibitor fluorohaloalkane in the vapor phase will also be in the specified range.

The application of this invention is illustrated in the following examples. The examples are not to be considered limiting in the broad sense of the invention but only by the scope of the appended claims.

EXAMPLE I

The tests enumerated in this Example were carried out to determine the stability of the various mixtures of CF$_2$ = CFOCH$_3$ when exposed to an electric spark compared to that of CF$_2$ = CFOCH$_3$ alone when tested under similar conditions.

The test procedure was as follows: approximately one ml of liquid was placed in a glass tube which was then closed tightly with a stopper having a copper wire passing through it and extending to a point several millimeters above the surface of the liquid. A high voltage induction coil was attached to a metal rod which was then placed against the outer surface of the tube. An alternating current spark (more properly an arc) approximately ⅜ inch long was then generated between the rod and the internal wire. When ignition (decomposition, reaction) took place there was a sharp report the instant the spark was generated and the cap was blown off the tube, leaving a deposit of carbon and brown residue on the inner surface of the tube. When the spark continued for ten seconds without decomposition occurring the system was considered to be stable. In tests 9, 12 and 15 the copper wire was actually immersed in the liquid. The tests were carried out at ambient temperature. The results are shown in Table I.

TABLE 1

| | CF$_2$ = CFOCH$_3$ STABILITY TESTS | | | |
|---|---|---|---|---|
| Test No. | CF$_2$ = CFOCH$_3$ in Mixture (b) % | CHFCl$_2$ in Mixture % | State of Material Tested | Reaction |
| 1 (a) | 98 | — | Liquid | No |
| 2 | 98 | — | Vapor | Yes |
| 3 | 98 | — | Vapor | Yes |
| 4 | 31 | 67 | Vapor | No |
| 5 | 39 | 59 | Vapor | No |
| 6 | 39 | 59 | Vapor | No |
| 7 | 44 | 54 | Vapor | No |
| 8 | 44 | 54 | Vapor | No |
| 9 | 42 | 56 | Liquid | No |

TABLE 1-continued
$CF_2=CFOCH_3$ STABILITY TESTS

| Test No. | $CF_2=CFOCH_3$ in Mixture (b) % | $CHFCl_2$ in Mixture % | State of Material Tested | Reaction |
|---|---|---|---|---|
| 10 | 42 | 56 | Vapor | No |

(a) Test carried out by arcing spark to outside of container without internal wire.
(b) 2% reaction product impurities (mostly $CF_2HCF_2OCH_3$) present in $CH_3O\,CF=CF_2$ in tests 1-10.

| Test No. | $CF_2=CFOCH_3$ in Mixture % | $CF_2ClCF_2Cl$ in Mixture % | $CFCl_3$ in Mixture % | State of Material Tested | Reaction |
|---|---|---|---|---|---|
| 11 | 47 | 53 | — | Vapor | No |
| 12 | 47 | 53 | — | Liquid | No |
| 13 | 49 | — | 51 | Vapor | Yes |
| 14 | 49 | — | 51 | Vapor | Yes |
| 15 | 49 | — | 51 | Liquid | No |

EXAMPLE II

Vapor Phase Deflagration

The object of Example II is to determine whether a condensed phase sample can be ignited at a high temperature site and can then sustain a propagating subsonic reaction to completion using a higher energy ignition source.

The limited concentration of the methyl trifluorovinyl ether in dichlorofluoromethane required for combustion was determine using stainless steel vessels of 350 cubic centimeters and about 10 liters volume. In performing the tests the appropriate quantities of methyl trifluorovinyl ether and dichlorofluoromethane are added to a previously evacuated vessel. After equilibration a nichrome coil ingiter is energised and pressure or temperature changes are noted by oscillograph. If deflagration does not occur under these conditions an electrically activated pyrotechnie igniter (squib) in then fired. The relative concentrations of the components are adjusted for subsequent trails until the deflagration or explosive limit is defined to ± 1%.

The results of the vapor phase deflagration study are presented in Table 2. The results indicate that for larger vessels the concentration limit would appear to be about 46% methyl trifluorovinyl ether in a mixture with the dichlorofluoromethane.

TABLE 2
Vapor Phase Deflagration
(Initial Pressure 14.2 ± 0.1 psia)

| Exp. No. | Temp. (°C) | Mol. % MTFVE | Mol. % CHFCl$_2$ | Weight % MTFVE | Weight % CHFCl$_2$ | Δ P (psi) | Reaction |
|---|---|---|---|---|---|---|---|
| 1 | 22 | 100 | 0 | 100 | 0 | 53 | Yes |
| 2 | 22 | 50 | 50 | 52.1 | 47.9 | 35 | Yes |
| 3 | 22 | 25 | 75 | 26.6 | 73.4 | 0 | No |
| 4 | 22 | 37.5 | 62.5 | 39.5 | 60.5 | 0 | No |
| 5 | 22 | 43.8 | 56.2 | 45.9 | 54.1 | 0 | No |
| 6 | 22 | 46.9 | 53.1 | 49.0 | 51.0 | 6 | Yes |
| 7 | 22 | 45.9 | 54.1 | 48.0 | 52.0 | 12 | Yes |
| 8 | 22 | 44.9 | 55.1 | 47.0 | 53.0 | 0 | No |
| 9 | 60 | 44.9 | 55.1 | 47.0 | 53.0 | 0 | No |
| 10 | 60 | 45.9 | 54.1 | 48.0 | 52.0 | 18 | Yes |
| 11 | 22 | 45.9 | 54.1 | 48.0 | 52.0 | * | Yes |
| 12 | 22 | 46.9 | 53.1 | 49.0 | 51.0 | * | Yes |
| 13 | 22 | 45.9 | 54.1 | 48.0 | 52.0 | 0 | No |
| 14 | 22 | 46.9 | 53.1 | 49.0 | 51.0 | 14 | Yes |

Exp. 1-10 in small vessels; exps. 11-14 in large vessels.
*Pressure recording system not functioning; go-no go decision based on residual attempt.
Pressure reading in psi is not realiable below about 15 psi in this system.

EXAMPLE III

Thermal Stability and Deflagration Potential of Liquid Phase

THe object of this example was to determine the response of a sample to extended exposure to high temperature under confinement. The thermal stability of liquid methyl trifluorovinyl ether was determined in admixture with dichlorofluoromethane with a nominal composition of 4/5 by weight a ratio considered to be in the safe range as determined in Example II. The thermal stability was examined in standard 340 cubic centimeters bombs. In the initial experiment a sample of the material mixture in the bomb was heated from room temperature at a rate of 1.0-1.5° C. per minute until an exotherm occurred.

In the thermal stability study conducted in the 340 cc bombs the pressures measured were 440 psia and 600 psia. In neither case was an exotherm detected. The critical pressure of the dichlorofluoromethane is 750 psia and a critical pressure of the methyl trifluorovinyl ether is 690 psia. The pressures measured were lower than expected and maybe due to the partial polymerization of the ether. If partial polymerization occurred it would be difficult to determine from pressure data whether or not the liquid phase was present up to the critical temperature.

In testing for deflagration potential the first test was made at atmospheric pressure. The test with the hot wire ignition source gave a small temperature and pressure rise higher than for no reaction but much below the normal expected to be obtained. There was physical evidence of some charring on the glass cup and bomb surfaces. However, there was a considerable amount of liquid left over indicating that the deflagration potential is low.

In a second test, the bomb was pressurized with nitrogen to about 250 psig to simulate inertial effects in large samples. There was no evidence of any significant temperature or pressure increase during the hot wire or squib firing of this nitrogen pressurized bomb. Much of the liquid was recovered from the bomb at the end of the experiment and it was concluded that no liquid phase deflagration occurred.

The second test was repeated at 250 psig nitrogen pressure and again no signs of deflagration were noted. From these data is concluded that liquid phase deflagration potential is minimal with the methyl trifluorovinyl ether in admixture with dichlorofluoromethane.

What I claim is:

1. Methyl trifluorovinyl ether stablized with respect to deflagration potential comprising methyl trifluorovinyl ether in admixture with one or more fluorohaloalkanes having a boiling point less than the boiling point of methyl trifluorovinyl ether.

2. The admixture of claim 1 in a weight ratio of fluorohaloalkane to methyl trifluorovinyl ether of 1:1 or greater.

3. The admixture of claim 1 wherein the fluorohaloalkane is selected from dichlorofluoromethane, 1,2-dichloro-1,1,2,2-tetrafluoroethane and mixtures thereof.

4. A mixture stabilized with respect to explosive potential comprising methyl trifluorovinyl ether in admixture with at least an equal weight of one or more fluorohaloalkanes having a vapor pressure at least as large as trifluorovinyl methyl ether under standard conditions.

5. The mixture of claim 4 wherein the fluorohaloalkane is selected from dichlorofluoromethane, 1,2-dichloro-1,1,2,2-tetrafluoroethane and mixtures thereof.

6. The mixture of claim 4 wherein the boiling point of the fluorohaloalkanes is less than the boiling point of methyl trifluorovinyl ether.

7. The mixture of claim 4 wherein the fluorohaloalkane is selected from the group consisting of dichlorofluoromethane; dichlorodifluoromethane; chlorodifluoromethane; trifluorobromomethane; trifluorochloromethane; 1,2-dichloro-1,1,2,2-tetrafluoroethane; pentafluorochloroethane; and mixtures thereof.

8. The admixture of claim 3 cooled to about 0° C. at about atmospheric pressure.

9. The admixture of claim 5 cooled to about 0° C. at about atmospheric pressure or less.

10. The admixture of claim 4 at an elevated pressure or a reduced temperature from ambient.

* * * * *